US012329993B2

(12) United States Patent
Hwang

(10) Patent No.: US 12,329,993 B2
(45) Date of Patent: Jun. 17, 2025

(54) EMERGENCY EVACUATION OXYGEN MASK

(71) Applicant: MAXENS Co., Ltd., Incheon (KR)

(72) Inventor: Jun Youn Hwang, Incheon (KR)

(73) Assignee: MAXENS Co., Ltd., Incheon (KR)

( * ) Notice: Subject to any disclaimer, the term of this patent is extended or adjusted under 35 U.S.C. 154(b) by 828 days.

(21) Appl. No.: 17/552,075

(22) Filed: Dec. 15, 2021

(65) Prior Publication Data
US 2023/0054808 A1 Feb. 23, 2023

(30) Foreign Application Priority Data

Aug. 18, 2021 (KR) .................. 10-2021-0108920

(51) Int. Cl.
A62B 18/02 (2006.01)
A62B 9/00 (2006.01)
A62B 25/00 (2006.01)
B65D 83/20 (2025.01)
A61M 15/00 (2006.01)

(52) U.S. Cl.
CPC .............. A62B 18/02 (2013.01); A62B 9/006 (2013.01); A62B 25/00 (2013.01); B65D 83/20 (2013.01); A61M 15/009 (2013.01); A63B 2213/005 (2013.01)

(58) Field of Classification Search
CPC ........... A62B 18/02; A62B 18/10; A62B 7/02; A62B 7/04; A62B 7/14; A62B 7/00; A62B 17/04; A62B 25/00; A62B 25/005; A61M 15/009; A63B 2213/005; B65D 83/205; B05B 1/00
See application file for complete search history.

(56) References Cited

U.S. PATENT DOCUMENTS 5,113,854 A * 5/1992 Dosch ...................... A62B 7/08
128/205.27
2008/0041375 A1* 2/2008 Stratton ................... A62B 7/00
128/203.23
2017/0362013 A1* 12/2017 Haage .................. B65D 47/261

FOREIGN PATENT DOCUMENTS

| KR | 10-1138310 B1 | 4/2012 |
| KR | 10-1578800 B1 | 1/2016 |
| KR | 10-2017-0092819 A | 8/2017 |
| KR | 10-1862089 B1 | 5/2018 |
| KR | 10-2019-0094756 A | 8/2019 |
| KR | 10-2236729 B1 | 4/2021 |

* cited by examiner

Primary Examiner — Timothy A Stanis
Assistant Examiner — Sara K Toich
(74) Attorney, Agent, or Firm — Hauptman Ham, LLP

(57) ABSTRACT

Proposed is an emergency evacuation oxygen mask provided with a hood configured to be worn on a user's head and an oxygen canister configured to supply oxygen to the user who wears the hood. The emergency evacuation oxygen mask includes an upper cover in which the hood is accommodated, a female coupling portion coupled to a lower end portion of the upper cover and connected to an oxygen supply port that is provided at the hood, and a male coupling portion provided on the oxygen canister and coupled to the female coupling portion, wherein when the upper cover or the oxygen canister is rotated, oxygen is discharged from the oxygen canister.

15 Claims, 16 Drawing Sheets

EMERGENCY EVACUATION OXYGEN MASK

CROSS REFERENCE TO RELATED APPLICATION

The present application claims priority to Korean Patent Application No. 10-2021-0108920, filed Aug. 18, 2021, the entire contents of which is incorporated herein for all purposes by this reference.

BACKGROUND OF THE INVENTION

Field of the Invention

The present disclosure relates to an emergency evacuation oxygen mask. More particularly, the present disclosure relates to an emergency evacuation oxygen mask configured to supply oxygen to a user during a time when the user evacuates to a safe place in an event of a disaster such as fire.

Description of the Related Art

Generally, a mask may be divided into a filter mask used at an industrial site where harmful gas and dust are generated and a mask provided with a self-contained breathing function used at a fire site and an oxygen deficit site such as a pit of a mine and the like.

The filter mask is configured to allow a wearer to breath by filtering toxic gas, dust generated at a working site, and the like through a purifying canister. The mask provided with the self-contained breathing function is configured to supply oxygen necessary for breathing to a wearer and to prevent the wearer from inhaling toxic gas at the same time.

Generally, the mask provided with the self-contained breathing function is provided with an oxygen tank in which compressed air is filled and a mask worn on the wearer's face. However, since a volume of the oxygen tank of the mask provided with the self-contained breathing function is high, there is a problem that mobility and portability are reduced, so that the mask provided with the self-contained breathing function is only applied to a professional person such as a fire-fighting officer who professionally extinguishes fire, and is limitedly used.

That is, the mask provided with the self-contained breathing function as described above may provide a suitable configuration for a fire-fighting officer who stays in a fire site for a long time and extinguishes fire, but has a deteriorated portability and a deteriorated mobility, so that there is a problem that the mask is difficult to be applied to an ordinary person. Particularly, it is very difficult for elderly people, children, and women to move to a safe place while carrying heavy oxygen tanks.

Therefore, in public facilities such as subway stations, airports, schools, buildings, and the like, and in homes, smoke masks using purifying canisters have been provided.

The smoke mask as described above does not use the oxygen tank with a high volume, so that there is an advantage that the portability and the mobility thereof are excellent, and there is also an advantage that the smoke mask is easy to put on.

However, the existing oxygen mask using the purifying canister has a configuration that is insufficient to secure the golden time in which the wearer moves to the safe place.

That is, the purifying canister of the smoke mask only has a configuration that blocks the toxic gas from being introduced into the smoke mask by using various known method such as a particle filtering method (filter), a chemisorption method (activated carbon), a chemical neutralization method (adding chemicals), and the like, and is not provided with an independent oxygen generation method and an oxygen supplying function.

The longer the movement time for the wearer to evacuate to the safe place, the lower the performance of the purifying canister. Therefore, there is a problem that the wearer suffers the anoxia and eventually suffocates. Particularly, when a fire occurs in a place where an oxygen concentration is low such as a subway station, a Korean dry sauna, or a basement of a building, the wearer suffers anoxia even if the purifying canister performs well. In fact, the oxygen mask using the purifying canister is designated by law so that the oxygen mask cannot be used at a place where an oxygen concentration is equal to or less than 17%.

In addition, when the evacuating route is complicated and long, it is difficult for elderly people, children, and women as well as healthy adult men to move by relying only on the smoke mask using the purifying canister, so that there is a problem that suffocation occurs due to toxic gas.

Particularly, when the wearer moves in location where the oxygen concentration is lowered while moving for evacuating to the safe place, the wearer suffers anoxia due to the insufficient oxygen concentration even if the wearer wears the smoke mask.

When the wearer suffers anoxia, it is difficult to make a calm and rational decision, and an athletic ability of the wearer is lowered depending on an exposure time, so that there is a problem that the wearer does not accurately determine the evacuating route and eventually suffocates while waiting at the current position.

Accordingly, in order to solve these problems, the present applicant has developed an oxygen mask and filed a patent application in which the oxygen mask is configured to supply only pure oxygen to a user during a time that the user moves to a safe place when a disaster such as fire occurs (Korean Patent Application No. 10-2020-0158172).

Meanwhile, the oxygen masks are stored in a pouch-type bag or a separate storage space, and is provided in homes, offices, public facilities, buildings, and the like. However, during an emergency situation such as fire, there is a problem that a putting on process after taking out the oxygen mask from the pouch-type bag or the storage space takes time and is difficult to perform.

Particularly, since the pouch-type bag is sealed so as to prevent external contamination, women or children have difficulty to open the pouch-type bag.

In addition, since the number of oxygen masks is insufficient due to the storage form of the oxygen mask as described above, the number of people who can actually use the oxygen mask during an emergency situation is very limited.

Accordingly, the present applicant developed the present disclosure in order to solve these problems as described above, and Korean Patent No. 10-1138310 "SELF-CONTAINED OXYGENATOR" as related conventional technology literature has been disclosed.

SUMMARY OF THE INVENTION

Accordingly, the present disclosure has been made keeping in mind the above problems occurring in the related art, and an objective of the present disclosure is to provide an emergency evacuation oxygen mask capable of being conveniently provided in structures such as homes, offices, public facilities, buildings, and the like, and also to provide an emergency evacuation oxygen mask capable of being rapidly and easily used by a wearer.

In addition, another objective of the present disclosure is to provide an emergency evacuation oxygen mask that does not deteriorate mobility of the wearer when the wearer is in a moving process for evacuating to a safe place while fire has occurred, and also to provide an emergency evacuation oxygen mask capable of supplying only pure oxygen to the wearer during only the golden time in which the wearer moves to the safe place.

According to an aspect of the present disclosure, there is provided an emergency evacuation oxygen mask including: a hood configured to be worn on a user's head; an oxygen canister configured to supply oxygen to the user who wears the hood; an upper cover in which the hood is accommodated; a female coupling portion coupled to a lower end portion of the upper cover and connected to an oxygen supply port that is provided at the hood; and a male coupling portion provided on the oxygen canister and coupled to the female coupling portion, wherein when the upper cover or the oxygen canister is rotated, oxygen may be discharged from the oxygen canister.

In addition, when the upper cover is rotated in one direction, the female coupling portion may be rotated in the one direction that is the same rotating direction of the upper cover, and the male coupling portion may be moved upward by a rotating force generated from the female coupling portion, so that a nozzle provided on the oxygen canister may be in contact with the female coupling portion.

In addition, the male coupling portion may include: a first body coupled to a circumference of an upper end portion of the oxygen canister; a protruding member protruding in a radial direction from an outer circumferential surface of the first body; a male tubular portion protruding upward from a top surface of the first body and surrounding the nozzle of the oxygen canister; and a guide groove provided at an outer surface of the male tubular portion.

In addition, the female coupling portion may include: a second body disposed on an upper portion of the first body; a cutout portion formed along an outer circumferential surface of the second body and into which the protruding member is inserted and caught; a rib protruding in the radial direction from the outer circumferential surface of the second body and connected to the upper cover; a female tubular portion protruding upward from a top surface of the second body and into which the male tubular portion is inserted; and a fastening protrusion provided at an inner circumferential surface of the female tubular portion and fastened to the guide groove.

In addition, the upper cover may include: a first groove formed at an inner circumferential surface of the lower end portion of the upper cover and into which the rib is inserted and accommodated; a second groove in communication with the first groove and providing a space where the protruding member inserted into the cutout portion is capable of being moved in a vertical direction; and a long hole in communication with the second groove and providing a space where the protruding member is capable of being moved in a horizontal direction.

In addition, the guide groove may include: a vertical section in which the fastening protrusion is moved in a vertical direction; a curved section in communication with the vertical section and in which the fastening protrusion is moved in a curved direction; a first horizontal section in communication with the curved section and in which the fastening protrusion is moved in a horizontal direction; and a second horizontal section having a width thereof smaller than a width of the first horizontal section and in communication with the first horizontal section, the second horizontal section being configured to limit a movement of the fastening protrusion.

In addition, the cutout portion may be formed toward an upper portion of the second body from a lower portion of the second body, and the cutout portion may be formed on the outer circumferential surface of the second body by being formed such that a first side portion of the cutout portion in a longitudinal direction is opened to the outside and a second side portion of the cutout portion in the longitudinal direction is blocked from the outside.

In addition, the second body may include: a stopper in contact with a first side portion of the protruding member in the longitudinal direction and configured to limit a movement of the protruding member; and a cam surface disposed to be spaced apart by a predetermined interval from the stopper and in contact with a second side portion of the protruding member in the longitudinal direction when the upper cover is rotated in the one direction or the oxygen canister is rotated in a direction opposite to the one direction.

In addition, the protruding member may be disposed between the stopper and the cam surface, and then the protruding member may be moved toward the second side portion of the cutout portion in the longitudinal direction.

In addition, the protruding member may be inserted into the long hole via the cutout portion.

In addition, when the protruding member is positioned at the second side portion of the cutout portion in the longitudinal direction as the upper cover is rotated in the one direction or as the oxygen canister or a lower cover is rotated in the direction opposite to the one direction, the second side portion of the protruding member in the longitudinal direction may be in contact with the rib.

In addition, the emergency evacuation oxygen mask may further include a lower cover configured to protect the oxygen canister, wherein an upper end of the lower cover may be detachably coupled to a lower end of the male coupling portion.

In addition, the emergency evacuation oxygen mask may further include a notification mechanism accommodated together with the hood inside the upper cover and configured to share information of the user with other person during an emergency situation, wherein the notification mechanism may include at least one of a light-emitting lamp, a speaker module, a GPS module, and a communication module.

In addition, the notification mechanism may be formed such that a through-hole with a predetermined diameter is provided at a first side of the notification mechanism, and a wire fixed to the hood may penetrate through the through-hole, so that the notification mechanism may be fixed without being separated from the hood.

In addition, a plurality of planes may be disposed along an outer circumferential surface of the upper cover, and two planes that are adjacent to each other may be disposed such that a predetermined angle is formed therebetween.

According to an embodiment of the present disclosure, the emergency evacuation oxygen mask is configured to supply oxygen to the user by an operation mechanism in which the upper cover is rotated in the one direction or the oxygen canister or the lower cover is rotated in the direction opposite to the one direction in a one-touch manner, so that the emergency evacuation oxygen mask is capable of being rapidly and easily used by anyone regardless of age and sex.

In addition, in the emergency evacuation oxygen mask according to an embodiment of the present disclosure, since a coupling structure between the guide groove and the fastening protrusion and a coupling structure between the cutout portion and the protruding member are provided in the emergency evacuation oxygen mask, unintentional rotations of the upper cover, the oxygen canister, and the lower cover may be doubly prevented, so that an accident in which the user is not able to be supplied with oxygen in an emergency situation may be prevented.

In addition, in the emergency evacuation oxygen mask according to an embodiment of the present disclosure, there is provided a configuration in which only pure oxygen is supplied to the wearer so as to prevent the wearer who wears the hood from suffering anoxia that occurs when an oxygen concentration is reduced in the fire site, so that the wearer may safely move to an evacuation place or may wait for a firefighter.

In addition, in the emergency evacuation oxygen mask according to an embodiment of the present disclosure, there is provided a configuration in which only pure oxygen is supplied during only in the golden time in which the wearer moves to the safe place or during only in the golden time in which the firefighter arrives, so that a size and a volume of a configuration supplying oxygen is simplified, so that mobility of the user and portability of the emergency evacuation oxygen mask may be increased.

In addition, in the emergency evacuation oxygen mask according to an embodiment of the present disclosure, since there is provided a configuration supplying oxygen to the wearer with a simplified structure, a manufacturing cost of the emergency evacuation oxygen mask is not expansive, so that a lot of emergency evacuation oxygen masks may be provided in public facilities such as schools, subway stations, airports, and the like.

In addition, in the emergency evacuation oxygen mask according to an embodiment of the present disclosure, although entire oxygen is exhausted to the inside of the hood from the oxygen canister, the wearer may take a spontaneous breath from inside the hood that forms a positive pressure, so that the golden time may be increased.

In addition, in the emergency evacuation oxygen mask according to an embodiment of the present disclosure, since there is provided a specific notification mechanism, various information related to the user may be transmitted to the outside during the emergency situation, so that rapid rescue of the user may be promoted.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Advantages and features of the present disclosure, and methods of achieving the same will become apparent with reference to the embodiments described below in detail in conjunction with the accompanying drawings. However, the present disclosure is not limited to the embodiments disclosed below, but may be implemented in various different forms. The present embodiments are intended to complete the disclosure of the present disclosure and provided to fully inform the skilled in the art to which the disclosure pertains of the scope of the disclosure. The disclosure is defined only by the scope of the claims.

Hereinafter, an emergency evacuation oxygen mask according to an embodiment of the present disclosure will be described in detail with reference to FIGS. 1 to 13. In a description of the present disclosure, a detailed description of related known functions or configurations will be omitted to avoid making the essence of the present disclosure unclear.

Figure 1:
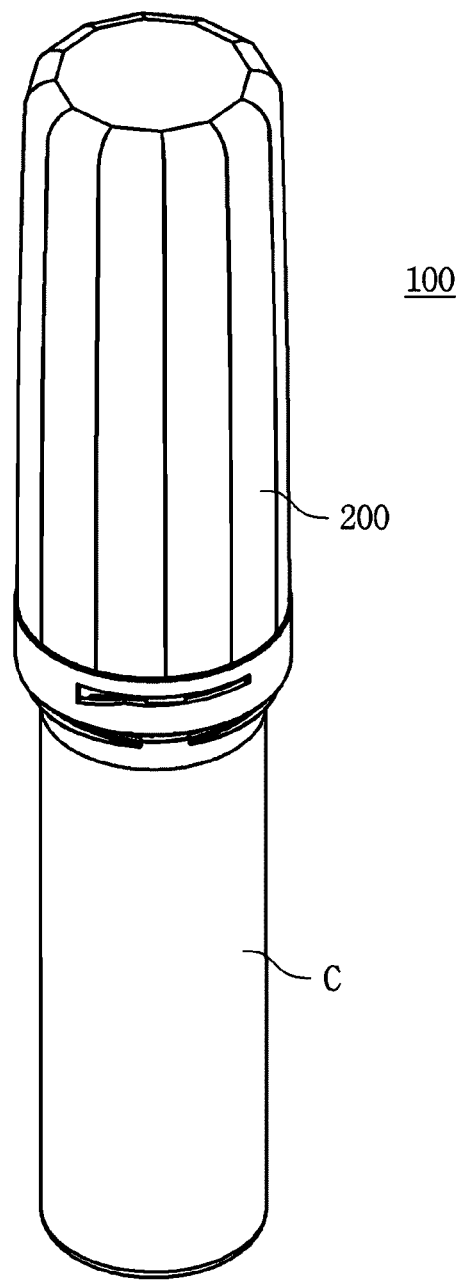
FIG. 1 is a perspective view illustrating an emergency evacuation oxygen mask according to an embodiment of the present disclosure.
Figure 2:
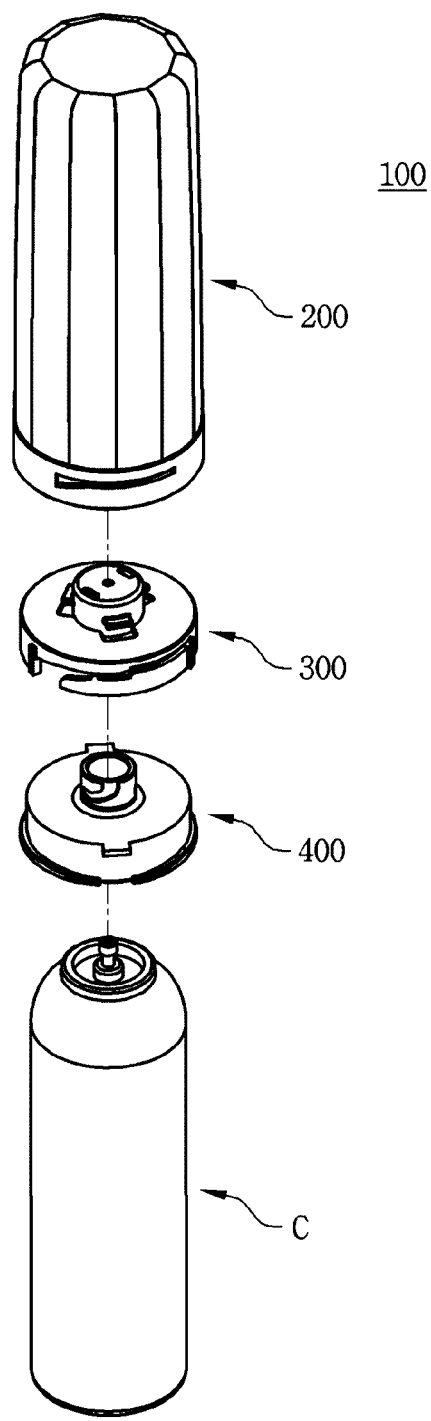
FIG. 2 is an exploded perspective view illustrating the oxygen mask illustrated in FIG. 1.
Figure 3:
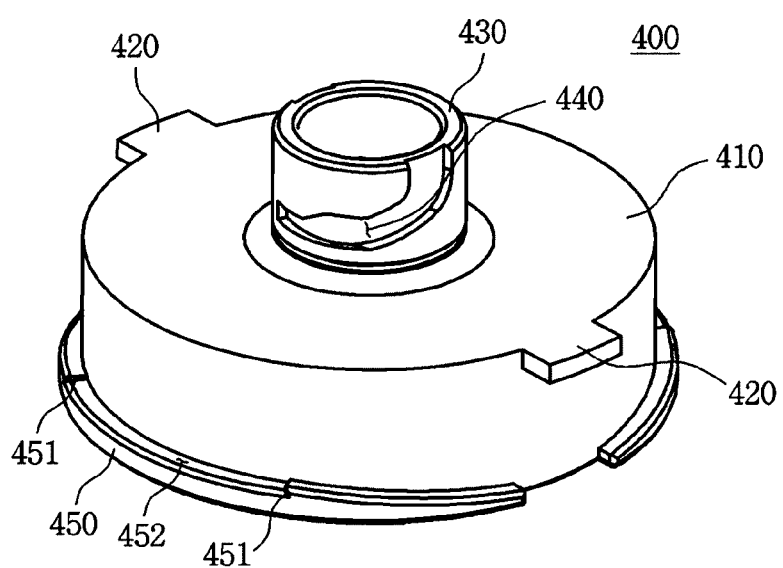
FIG. 3 is a perspective view illustrating a male coupling portion illustrated in FIG. 2.
Figure 4:
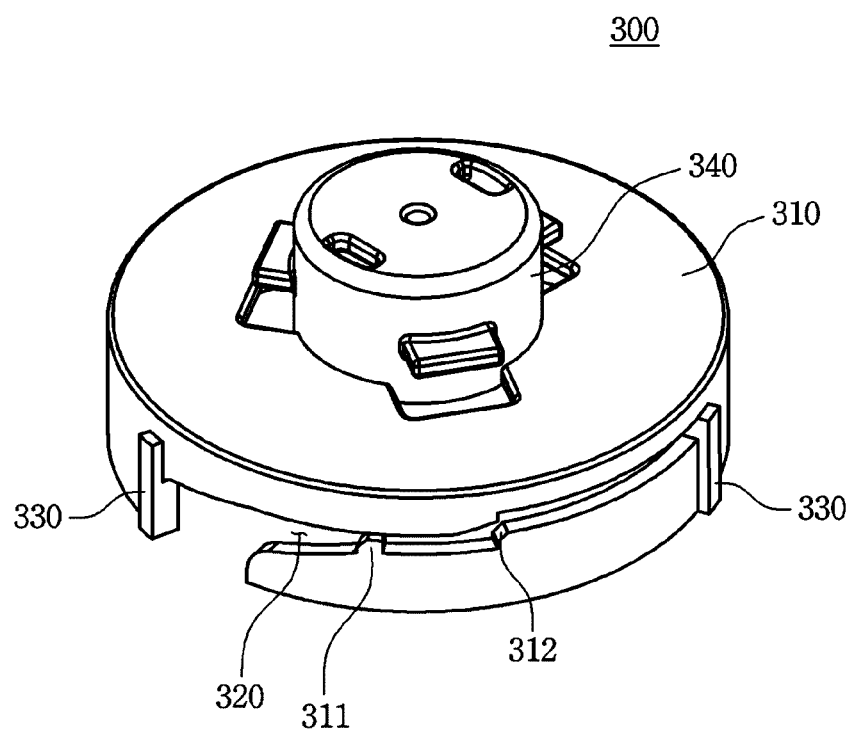
FIG. 4 is a perspective view illustrating a female coupling portion illustrated in FIG. 2.
Figure 5:
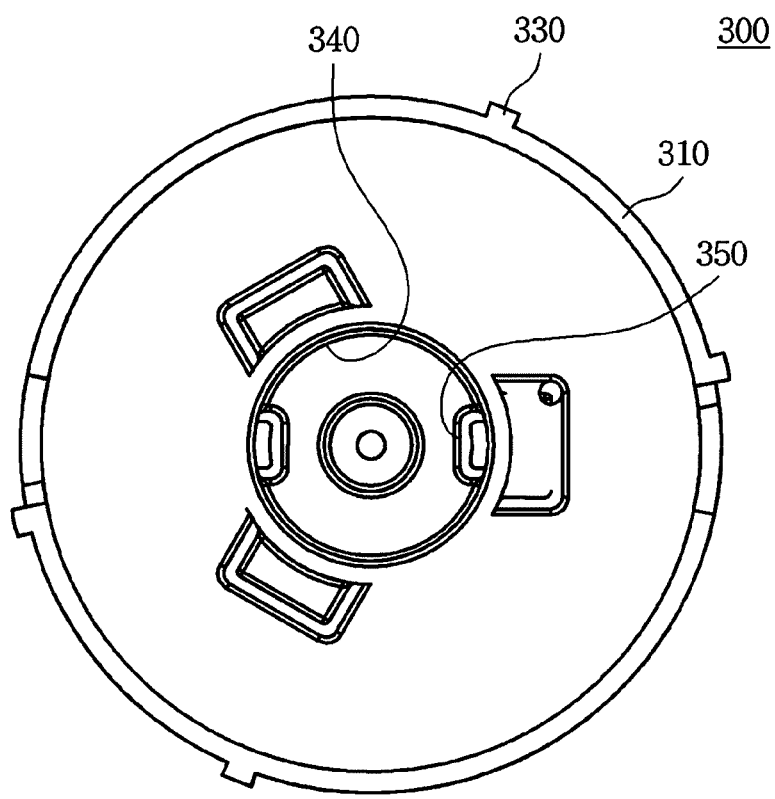
FIG. 5 is a bottom view illustrating the female coupling portion illustrated in FIG. 2.
Figure 6:
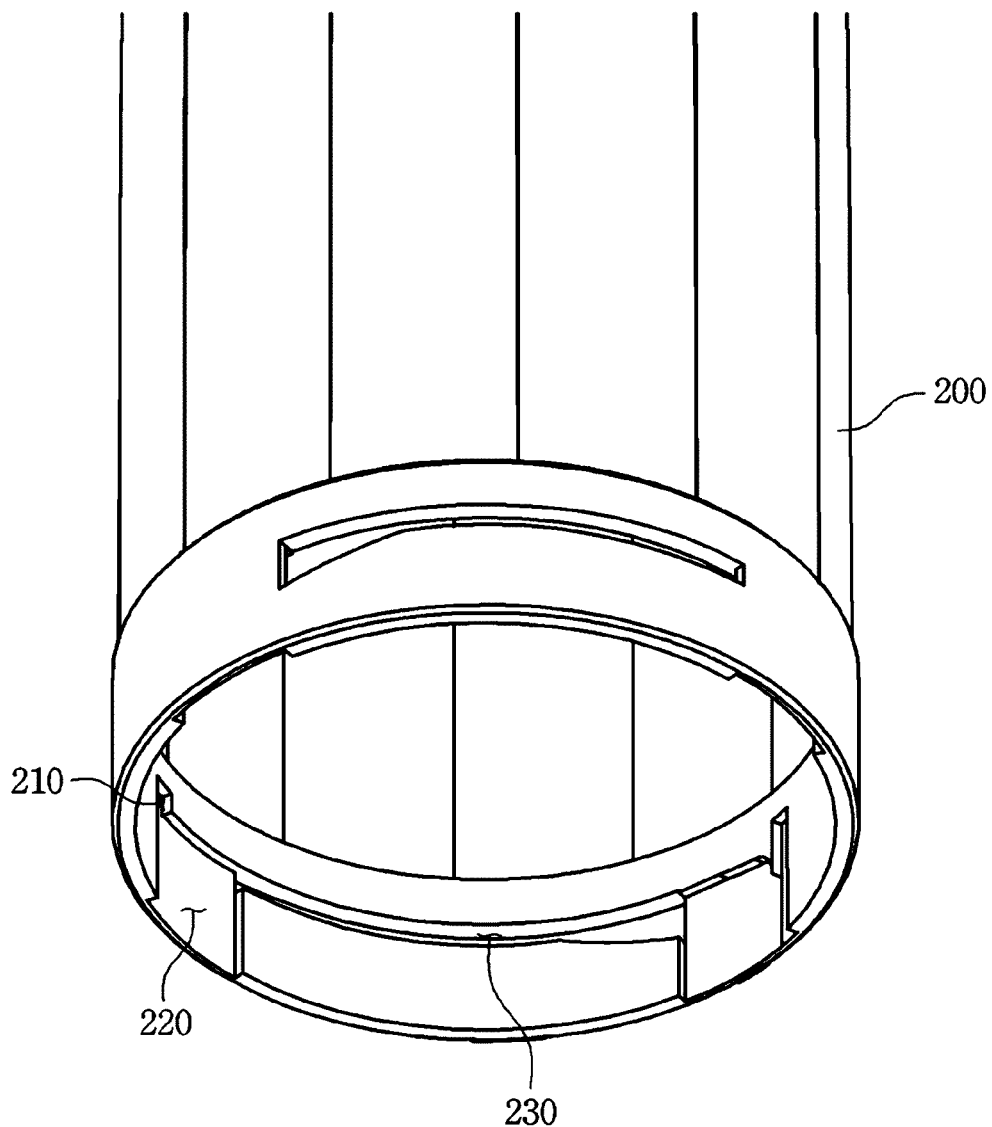
FIG. 6 is a perspective view illustrating an upper cover illustrated in FIG. 2 when viewed from a bottom portion.
Figure 7:
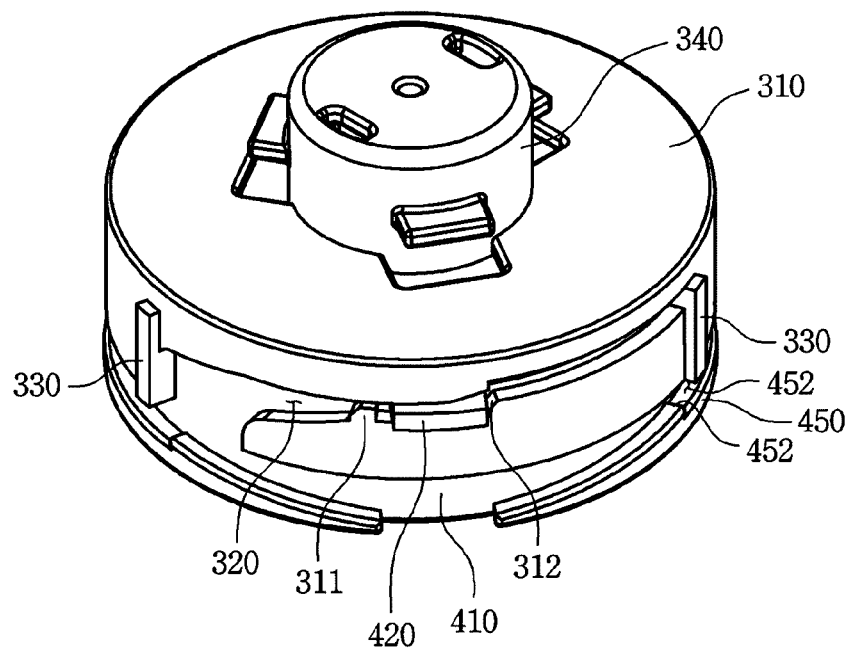
FIG. 7 is a perspective view illustrating a state in which the male coupling portion and the female coupling portion according to an embodiment of the present disclosure are coupled to each other.
Figure 8:
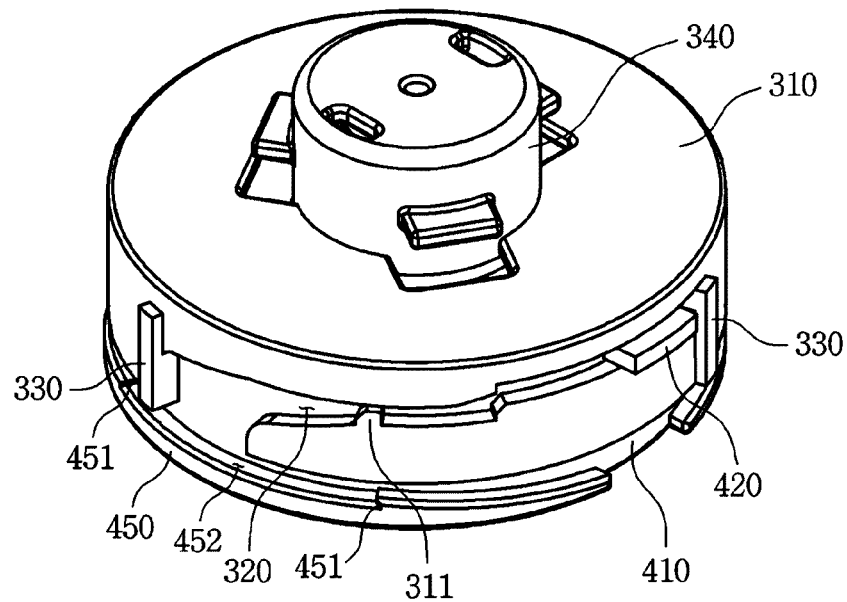
FIG. 8 is a perspective view illustrating that a protruding member illustrated in FIG. 7 is positioned at a second side of a cutout portion in a longitudinal direction.
Figure 9:
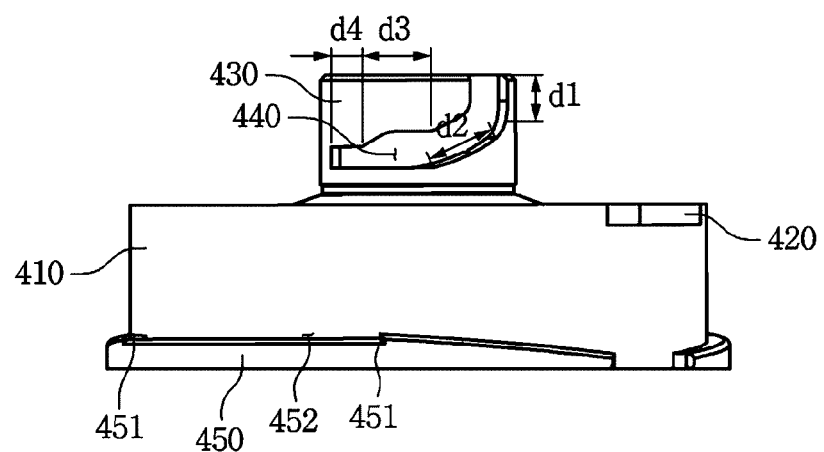
FIG. 9 is a perspective view illustrating a configuration of a guide groove according to an embodiment of the present disclosure.
Figure 10:
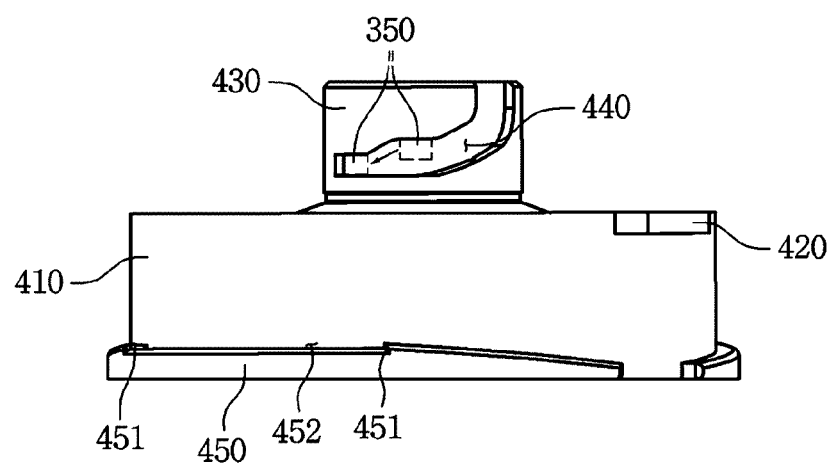
FIG. 10 is a view illustrating a process in which a fastening protrusion according to an embodiment of the present disclosure is moved along the guide groove.
Figure 11:
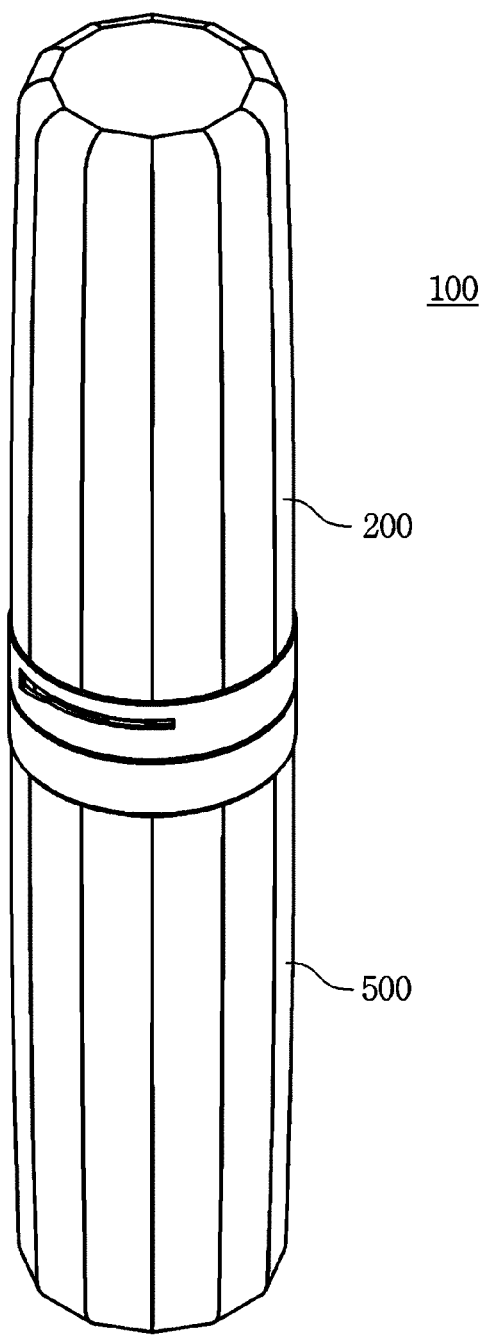
FIG. 11 is a perspective view illustrating a state in which the male coupling portion according to an embodiment of the present disclosure is mounted on a lower cover.
Figure 12:
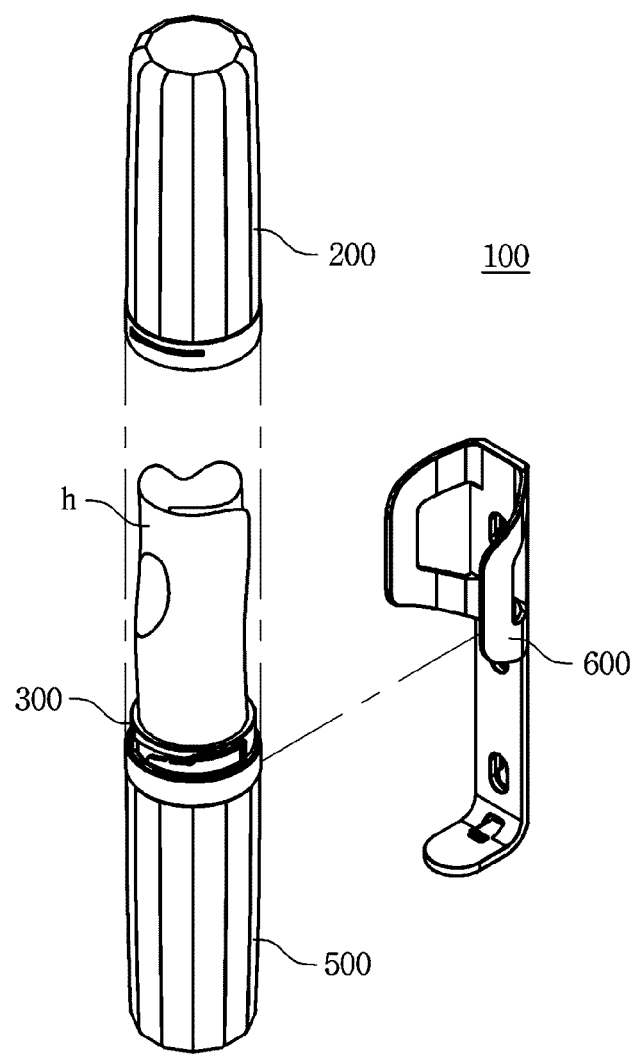
FIG. 12 is a perspective view illustrating that a hood is provided on the female coupling portion according to an embodiment of the present disclosure.
Figure 13:
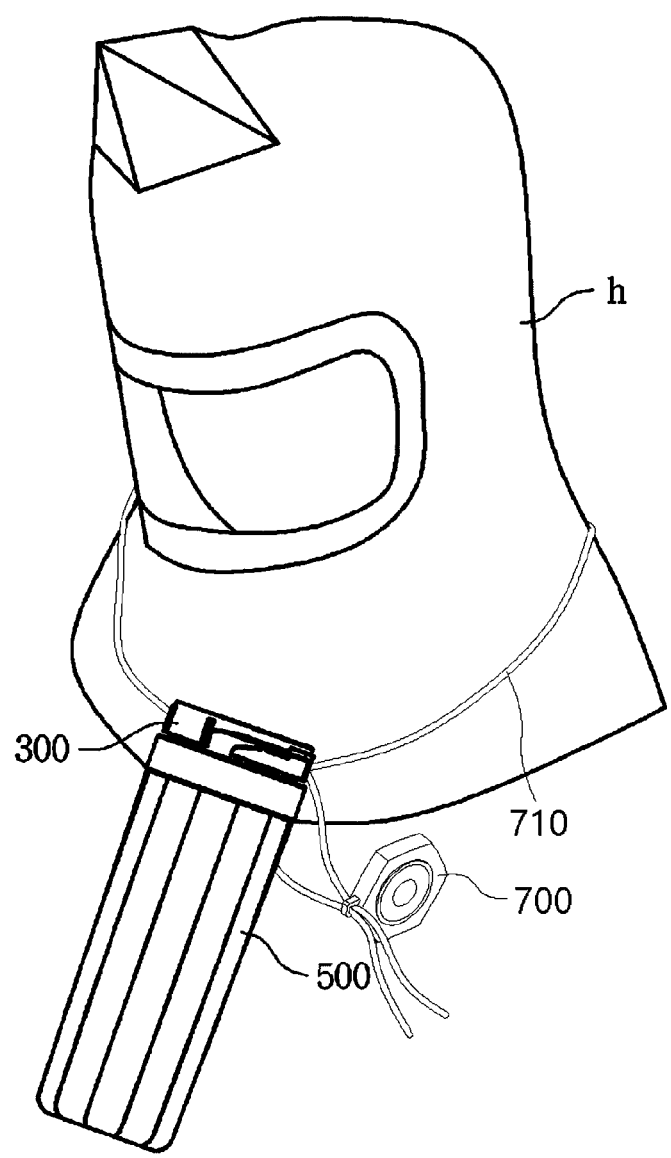
FIG. 13 is a perspective view illustrating a usage state of the emergency evacuation oxygen mask according to an embodiment of the present disclosure.
Figure 14:
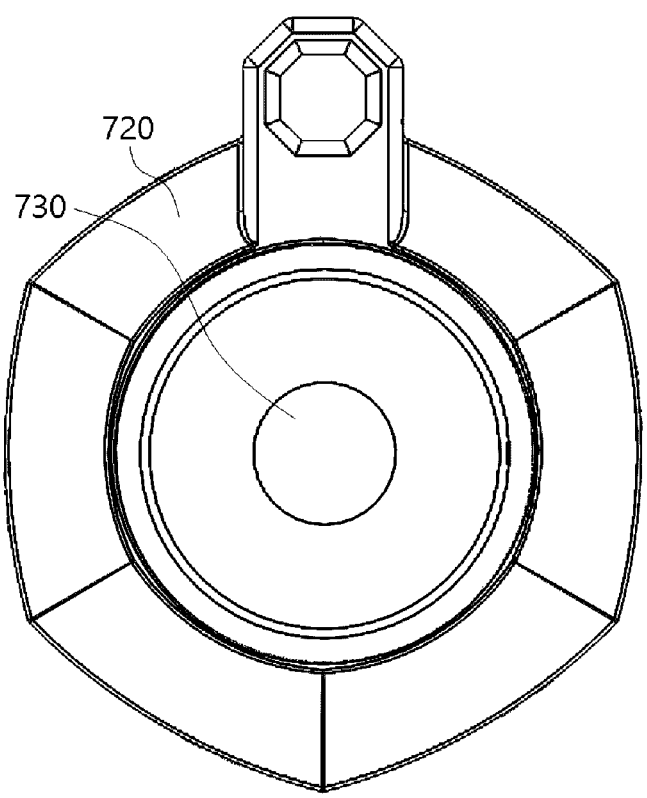
FIGS. 14 and 15 are views illustrating an upper portion and a lower portion of a notification mechanism according to an embodiment of the present disclosure.
Figure 15:
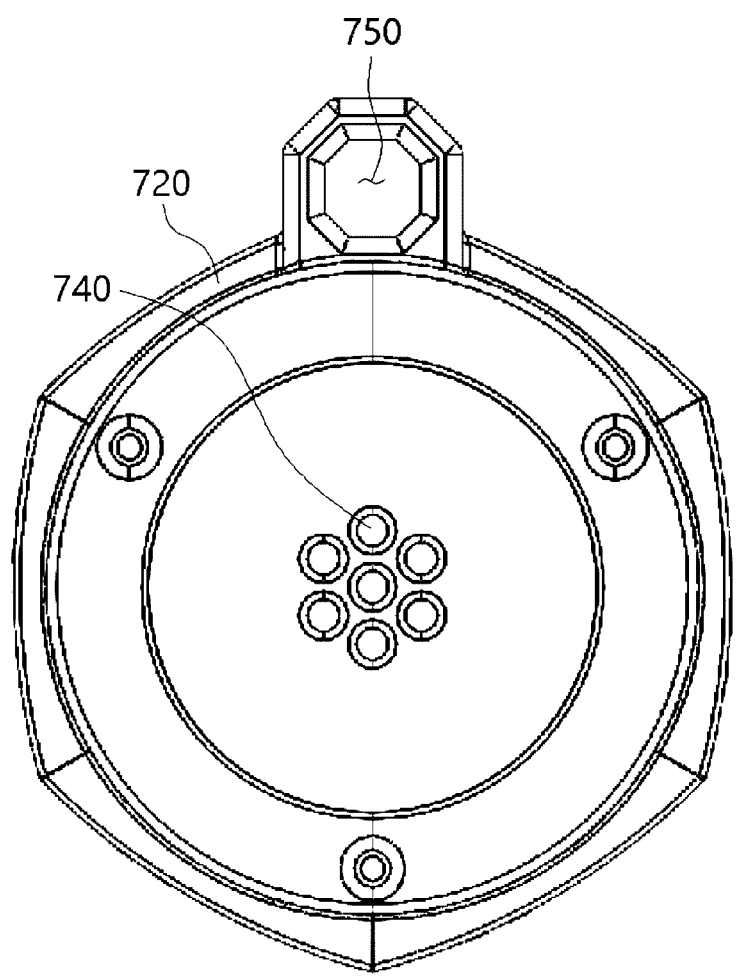
Figure 16:
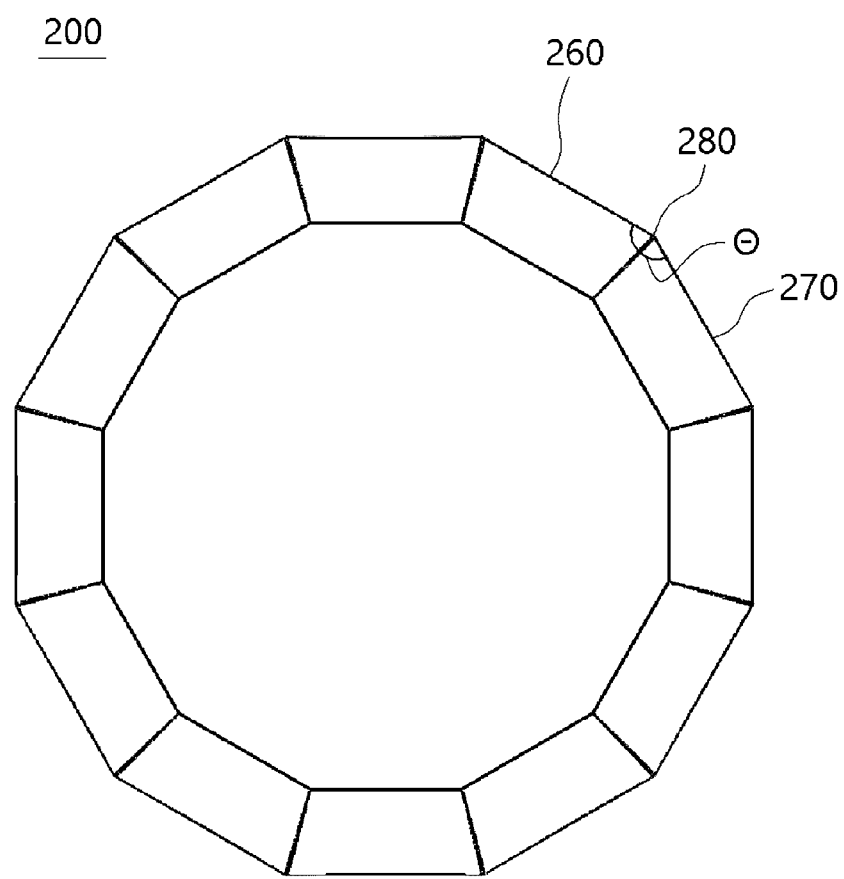
FIG. 16 is a plan view illustrating the upper cover according to an embodiment of the present disclosure when viewed from above.

FIG. 1 is a perspective view illustrating an emergency evacuation oxygen mask according to an embodiment of the present disclosure. FIG. 2 is an exploded perspective view illustrating the oxygen mask illustrated in FIG. 1. FIG. 3 is a perspective view illustrating a male coupling portion illustrated in FIG. 2. FIG. 4 is a perspective view illustrating a female coupling portion illustrated in FIG. 2. FIG. 5 is a bottom view illustrating the female coupling portion illustrated in FIG. 2. FIG. 6 is a perspective view illustrating an upper cover illustrated in FIG. 2 when viewed from a bottom portion. FIG. 7 is a perspective view illustrating a state in which the male coupling portion and the female coupling portion according to an embodiment of the present disclosure are coupled to each other. FIG. 8 is a perspective view illustrating that a protruding member illustrated in FIG. 7 is positioned at a second side of a cutout portion in a longitudinal direction. FIG. 9 is a perspective view illustrating a configuration of a guide groove according to an embodiment of the present disclosure. FIG. 10 is a view illustrating a process in which a fastening protrusion according to an embodiment of the present disclosure is moved along the guide groove. FIG. 11 is a perspective view illustrating a state in which the male coupling portion according to an embodiment of the present disclosure is mounted on a lower cover. FIG. 12 is a perspective view illustrating that a hood is provided on the female coupling portion according to an embodiment of the present disclosure. FIG. 13 is a perspective view illustrating a usage state of the emergency evacuation oxygen mask according to an embodiment of the present disclosure. In addition, FIGS. 14 and 15 are views illustrating an upper portion and a lower portion of a notification mechanism according to an embodiment of the present disclosure, and FIG. 16 is a plan view illustrating the upper cover according to an embodiment of the present disclosure when viewed from above.

In an emergency evacuation oxygen mask according to an embodiment of the present disclosure, as an example, there may be an advantage that only pure oxygen is supplied to a user so as to prevent an oxygen concentration of the user from being lowered during the golden time so that the user does not suffer from anoxia during a time it takes for the user to arrive at a safe evacuation place or during a time it takes for a firefighter to arrive at a fire site when a fire has occurred. Particularly, the emergency evacuation oxygen mask of the present disclosure is configured such that a person without distinction of age or sex is capable of rapidly and easily using the emergency evacuation oxygen mask of the present disclosure, and many emergency evacuation oxygen masks of the present disclosure may be stored or provided in homes, schools, offices, buildings, subway stations, subway trains, etc.

As illustrated in FIGS. 1 and 2, the emergency evacuation oxygen mask 100 as described above may include: a hood h (see FIG. 12 and FIG. 13) configured to be worn on a user's head; an oxygen canister c configured to provide oxygen to the user who wears the hood h; an upper cover 200 in which the hood h is accommodated; a female coupling portion 300 coupled to a lower end portion of the upper cover 200 and connected to an oxygen supply port (not illustrated) that is provided at the hood h; and a male coupling portion 400 coupled to the female coupling portion 300 while being provided on the oxygen canister c.

In the oxygen mask 100 according to an embodiment of the present disclosure, when the user rotates the upper cover 200, the oxygen canister c, or a lower cover 500 that will be described later, oxygen stored in the oxygen canister c is provided to the user.

First, as illustrated in FIG. 3, the male coupling portion 400 may include: a first body 410 coupled to a circumference of an upper end portion of the oxygen canister c; a protruding member 420 protruding in a radial direction from an outer circumferential surface of the first body 410; a male tubular portion 430 protruding upward from a top surface of the first body 410 and configured to surround a nozzle of the oxygen canister c; and a guide groove 440 provided at an outer surface of the male tubular portion 430.

The first body 410 has a cylindrical shape as a whole, and a lower portion thereof is opened such that the upper end portion of the oxygen canister c is inserted into the lower portion of the first body 410.

A plurality of protruding members 420 may be provided on the outer circumferential surface of the first body 410 with being spaced apart from each other. In an embodiment of the present disclosure, it is illustrated in the drawings that two protruding members 420 are spaced apart from each other and are provided on the outer circumferential surface of the first body 410.

The male tubular portion 430 may be formed in a hollowed tube shape surrounding the nozzle that is provided on the oxygen canister c, and may be referred to as a component that is directly fastened to the female coupling portion 300. That is, the male tubular portion 430 protects the nozzle formed on the upper end of the oxygen canister c and also enables the nozzle of the oxygen canister c to be in communication with the oxygen supply port (not illustrated) that is formed on the hood h.

The guide groove 440 may be formed along a circumferential surface of the male tubular portion 430. In an embodiment of the present disclosure, two guide grooves 440 may be formed on the outer surface of the male tubular portion 430 with being spaced apart from each other.

In addition, as illustrated in FIGS. 9 and 10, the guide groove 400 may include: a vertical section d1 in which a fastening protrusion 350 (see FIG. 5) of the female coupling portion 300 that will be described later is moved in a vertical direction; a curved section d2 in communication with the vertical section d1 and in which the fastening protrusion 350 is moved in a curved direction; a first horizontal section d3 in communication with the curved section d2 and in which the fastening protrusion 350 is moved in a horizontal direction; and a second horizontal section d4 having a width thereof smaller than a width of the first horizontal section d3 and in communication with the first horizontal section d3, the second horizontal section d4 being configured to limit a movement of the fastening protrusion 350.

The vertical section d1 is a section in which the fastening protrusion 350 of the female coupling portion 300 is inserted and moved in the vertical direction when the female coupling portion 300 and the male coupling portion 400 are initially coupled to each other. More specifically, the vertical section d1 is a section in which the fastening protrusion 350 is moved along a height direction of the male tubular portion 430 on which the guide groove 440 is formed.

The fastening protrusion 350 disposed on the vertical section d1 cannot be moved in a circumferential direction of the male tubular portion 430. This is because the movement of the fastening protrusion 350 is blocked by side walls that define the vertical section d1.

The curved section d2 may be referred to as a section that changes a moving direction of the fastening protrusion 350 that is inserted into the vertical section d1 into the horizontal direction.

The first horizontal section d3 may be referred to as a section in which the fastening protrusion 350 passing through the curved section d2 is moved in the horizontal direction. More accurately, the first horizontal section d3 may be referred to as a section in which the fastening protrusion 350 is moved along the circumferential direction of the male tubular portion 430.

The fastening protrusion 350 disposed on the first horizontal section d3 cannot be moved in the vertical direction. This is because the movement of the fastening protrusion 350 is blocked by an upper wall and a lower wall that define the first horizontal section d3. Therefore, when the fastening protrusion 350 reaches the first horizontal section d3, the male tubular portion 430 maintains a coupled state with a female tubular portion 340 (see FIG. 4) that will be described later, and is not separated from the female tubular portion 340.

Meanwhile, the width of the first horizontal section d3 is larger than a width of the fastening protrusion 350. Therefore, although the male tubular portion 430 may maintain the coupled state that is not separated from the female tubular portion 340, shaking may occur in an up and down direction since the width of the first horizontal section d3 and the width of the fastening protrusion 350 are different from each other. However, this shaking situation may be prevented by the protruding member 420 that is inserted into a cutout portion 320 (see FIG. 7) of the female coupling portion 300 that will be described later.

The second horizontal section d4 may be referred to as a section in which the fastening protrusion 350 passing through the first horizontal section d3 is inserted and moved in the horizontal direction, and an end portion at a first side of the second horizontal section d4 is blocked. That is, the second horizontal section d4 may be referred to as a section in which the fastening protrusion 350 finally arrives.

Meanwhile, the width of the second horizontal section d4 may be smaller than the width of the first horizontal section d3. In addition, the width of the second horizontal section d4 may be equal to or larger than the width of the fastening protrusion 350. Therefore, the shaking situation in the up and down direction may be further minimized when the fastening protrusion 350 passing through the first horizontal section d3 is moved to the second horizontal section d4 from the first horizontal section d3. For example, the fastening protrusion 350 may be inserted into the second horizontal section d4 in a forcibly fitting manner. Meanwhile, a first side portion of the first horizontal section d3 in the longitudinal direction in communication with the second horizontal section d4 has a shape in which the width gradually decreases toward the second horizontal section d4 such that the fastening protrusion 350 is easily introduced into the second horizontal section d4.

Similarly, the movement in the vertical direction of the fastening protrusion 350 may be blocked by an upper wall and a lower wall that define the second horizontal section d4. At this time, as described above, since the width of the second horizontal section d4 is smaller than the width of the first horizontal section d3 and is equal to or larger than the width of the fastening protrusion 350, the male tubular portion 430 is securely coupled to the female tubular portion 340 without being shaken when the fastening protrusion 350 is moved to the second horizontal section d4.

As illustrated in FIGS. 4 and 5, the female coupling portion 300 may include: a second body 310 disposed on the upper portion of the first body 410; the cutout portion 320 formed along an outer circumferential surface of the second body 310 and into which the protruding member 420 is inserted and caught; a rib 330 protruding in the radial direction from the outer circumferential surface of the second body 310 and connected to the upper cover 200; the female tubular portion 340 protruding upward from a top surface of the second body 310 and into which the male tubular portion 430 is inserted; and the fastening protrusion 350 provided at an inner circumferential surface of the female tubular portion 340 and fastened to the guide groove 440.

The second body 310 has a cylindrical shape as a whole, and a lower end portion thereof is opened such that the first body 410 is inserted into the lower end portion of the second body 310.

The cutout portion 320 is formed along a circumferential surface of the second body 310, and the number of the cutout portions 320 may correspond to the number of the protruding members 420 that are provided on the first body 410. In an embodiment of the present disclosure, two cutoff portions 320 are formed on the circumferential surface of the second body 310 with being spaced apart from each other.

In addition, the cutout portion 320 may be formed on the outer circumferential surface of the second body 310 toward the upper portion of the second body 310 from a lower portion of the second body 310 by being formed such that a first side portion in a longitudinal direction thereof is opened to the outside and a second side portion in the longitudinal direction thereof is blocked from the outside.

A plurality of ribs 330 may be formed on the outer circumferential surface of the second body 310 with being spaced apart from each other, and may be formed along a height direction of the second body 310. In an embodiment of the present disclosure, it is illustrated in the drawings that the ribs 330 are respectively disposed on the first side portion and the second side portion of the cutout portion 320 in the longitudinal direction.

The female tubular portion 340 may be referred to as a member that is connected to the hood h, and is provided with an internal space into which the male tubular portion 430 may be inserted.

The fastening protrusion 350 protrudes toward a center of the female tubular portion 340 from the inner circumferential surface of the female tubular portion 340, and the number of the fastening protrusions 350 may correspond to the number of the guide grooves 440 that are formed on the outer surface of the male tubular portion 430. In an embodiment of the present disclosure, two fastening protrusions 350 are formed with being spaced apart from each other.

As illustrated in FIG. 6, the upper cover 200 may be formed in the cylindrical shape in which an upper end of the shape is blocked from the outside and a lower end of the shape is provided with an opened portion, and the lower end portion of the shape may be detachably coupled to the female coupling portion 300.

In addition, referring to FIG. 16, a plurality of planes 260 and 270 is disposed along an outer circumferential surface of the upper cover 200, and two planes 260 and 270 that are adjacent to each other may form a predetermined angle Θ therebetween. That is, an angled portion 280 may be formed on the outer surface of the upper cover 200 where the user holds. For an example, as illustrated in FIG. 16, the upper cover 200 may be formed in a regular polygonal shape. Through this, when the user rotates the upper cover 200 during an emergency situation, the upper cover 200 is capable of being stably and rapidly rotated in a clockwise direction or a counter-clockwise direction without slipping.

In addition, the upper cover 200 may include: a first groove 210 formed on a lower end portion of the inner circumferential surface of the upper cover 200 and in which the rib 330 of the female coupling portion 300 is inserted and accommodated; a second groove 220 in communication with the first groove 210 and providing a space where the protruding member 420 inserted into the cutout portion 320 is capable of being moved in the vertical direction; and a long hole 230 in communication with the second groove 220 and providing a space where the protruding member 420 is capable of being moved in the horizontal direction.

The number of the first grooves 210 may correspond to the number of the ribs 330 that are provided on the female coupling portion 300.

The second groove 220 is configured to prevent the upper cover 200 from being interfering with the protruding member 420 of the male coupling portion 400 when the upper cover 200 is coupled to or separated from the female coupling portion 300. That is, the second groove 220 provides the space where the protruding member 420 is capable of being moved.

The long hole 230 provides the space into which the protruding member 420 inserted into and caught on the cutout portion 320 is inserted, and also provides the space where upper cover 200 is capable of being rotated without being interfering with the protruding member 420.

By the upper cover 200, the female coupling portion 300, and the male coupling portion 400 that are configured as described above, when the upper cover 200 is rotated in one direction, the female coupling portion 300 is capable of being rotated in the one direction that is the same rotating direction of the upper cover 200.

At this time, the male coupling portion 400 is moved upward by rotating force generated from the female coupling portion 300, and enables the nozzle provided on the oxygen canister c to be in contact with a ceiling surface of the female tubular portion 340. That is, the oxygen canister c is moved upward together with the male coupling portion 400, so that the oxygen canister c may discharge oxygen while the nozzle provided on the upper end of the oxygen canister c is in contact with the ceiling surface of the female tubular portion 340. Oxygen discharged through the nozzle passes through a hole formed on a center of the female tubular portion 340 and passes through the oxygen supply port of the hood h, and is delivered to the user.

The female coupling portion 300 and the male coupling portion 400 may be coupled to each other as illustrated in FIGS. 7 and 8. That is, the male coupling portion 400 may be inserted into the internal space that is formed by the female coupling portion 300.

At this time, as illustrated in FIG. 7, the protruding member 420 of the male coupling portion 400 may be inserted into the cutout portion 320 from the first side portion of the cutout portion 320 in the longitudinal direction, and then may be positioned at a middle portion of the cutout portion 320 in the longitudinal direction.

As described above, when the protruding member 420 is positioned at the middle portion of the cutout portion 320 in the longitudinal direction, the nozzle of the oxygen canister c is in a state of being non-contact with the ceiling surface of the female tubular portion 340. Therefore, it may be referred to as a state in which oxygen is not supplied inside the hood h.

Meanwhile, as illustrated in FIG. 4 and FIG. 7, the second body 310 may include: a stopper 311 in contact with the first side portion of the protruding member 420 in the longitudinal direction and configured to limit the movement of the protruding member 420; and a cam surface 312 spaced apart from the stopper by a predetermined interval and configured to be in contact with the second side portion of the protruding member 420 in the longitudinal direction when the upper cover 200 is rotated in the one direction or the oxygen canister c is rotated in an opposite direction.

That is, the protruding member 420 inserted into the cutout portion 320 from the first side of the cutout portion 320 in the longitudinal direction and moved to the middle portion of the cutout portion 320 in the longitudinal direction is in a state of being disposed on a space between the stopper 311 and the cam surface 312.

By the configuration as described above, when the upper cover 200 moves in the clockwise direction, the second body 310 of the male coupling portion 300 is rotated in the clockwise direction in conjunction with the upper cover 200. At this time, the cam surface 312 of the second body 310 may be in sliding contact with the second side portion of the protruding member 420 in the longitudinal direction.

In contrast, even when the oxygen canister c is rotated in the counter-clockwise direction or the lower cover 500 that will be described later is rotated in the counter-clockwise direction, the cam surface 312 of the second body 310 may be in sliding contact with the second side portion of the protruding member 420 in the longitudinal direction.

Then, as illustrated in FIG. 8, the protruding member 420 is in a state of being positioned at the second side of the cutout portion 320 in the longitudinal direction. Meanwhile, since the cutout portion 320 is formed toward the upper portion of the second body 310 from the lower portion of the second body 310, the protruding member 420 is positioned at the second side of the cutout portion 320 in the longitudinal direction while being moved upward. At this time, the second side portion of the protruding member 420 in the longitudinal direction is in contact with the rib 300 formed on the outer circumferential surface of the second body 310, so that the movement of the protruding member 420 may be limited. That is, since the rib 330 formed on the outer circumferential surface of the second body 310 is in contact with the second side portion of the protruding member 420 in the longitudinal direction, a rotation movement in the clockwise direction between the upper cover 200 and the female coupling portion 300 and a rotation movement in the counter-clockwise direction between the oxygen canister c and the lower cover 500 may be limited.

By the operation process as described above, an interval between the female coupling portion 300 and the male coupling portion 400 may be reduced. That is, when the protruding member 420 is positioned at the second side of the cutout portion 320 in the longitudinal direction, the interval between the female coupling portion 300 and the male coupling portion 400 is reduced, so that the nozzle of the oxygen canister c is in a state of being in contact with the ceiling surface of the female tubular portion 340. Therefore, it may be referred to as a state in which oxygen is supplied inside the hood h.

Meanwhile, when the female coupling portion 300 and the male coupling portion 400 are coupled to each other as illustrated in FIG. 7, as illustrated in FIGS. 9 and 10, the fastening protrusion 350 formed on the inner circumferential surface of the female tubular portion 340 may be positioned at the first horizontal section d3 by being sequentially passing through the vertical section d1 and the curved section d2 of the guide groove 440.

When the fastening protrusion 350 is positioned at the first horizontal section d3, the nozzle of the oxygen canister c is in a state of being in non-contact with the ceiling surface of the female tubular portion 340. Therefore, it may be referred to as a state in which oxygen is not supplied inside the hood h.

When the upper cover 200 is rotated in the clockwise direction or the lower cover 500 that will be described later is rotated in the counter-clockwise direction, the fastening protrusion 350 positioned at the first horizontal section d3 may be moved to the second horizontal section d4, as illustrated in FIG. 10.

In the state as described above, the interval between the female coupling portion 300 and the male coupling portion 400 may be reduced. That is, when the fastening protrusion 350 is positioned at the second horizontal section d4 of the guide groove 440, the interval between the female coupling portion 300 and the male coupling portion 400 is reduced, so that the nozzle of the oxygen canister c is in a state of being in contact with the ceiling surface of the female tubular portion 340. Therefore, it may be referred to as a state in which oxygen is supplied inside the hood h.

In the emergency evacuation oxygen mask according to an embodiment of the present disclosure, oxygen is capable of being provided inside the hood h with an easy operating mechanism in which the upper cover 200 is rotated in the clockwise direction or the oxygen canister c or the lower cover 500 that will be described later is rotated in the counter-clockwise direction, so that there is an advantage that anyone can easily use the emergency evacuation oxygen mask of the present disclosure.

In addition, the emergency evacuation oxygen mask 100 according to an embodiment of the present disclosure may further include the lower cover 500 detachably coupled to the circumferential surface of the lower end of the male coupling portion 400.

The lower cover 500 is configured to protect the oxygen canister c. Further, as illustrated in FIG. 12, the lower cover 500 is detachably coupled to a holder 600, so that the emergency evacuation oxygen mask 100 according to an embodiment of the present disclosure may be easily stored in or provided in homes, offices, public facilities, buildings, and the like.

Meanwhile, on the circumferential surface at the lower end of the first body 410, a locking portion 450 coupled to a fastening member (not illustrated) that is formed on the inner circumferential surface at the upper end of the lower cover 500 may be formed along the circumferential direction of the first body 410.

On the locking portion 450, a rail groove 452 into which the fastening member (not illustrated) of the lower cover 500 is inserted may be formed at a predetermined depth, and locking jaws 451 are respectively formed on opposite sides of the rail groove 452 in the longitudinal direction.

Therefore, when the lower cover 500 is rotated in the counter-clockwise direction, the fastening member (not illustrated) inserted into the rail groove 452 is moved in the counter-clockwise direction and the fastening member (not illustrated) is in a state of being in contact with the locking jaw 451, and the first body 410 is capable of being rotated in the counter-clockwise direction in conjunction with the state as described above.

Meanwhile, referring to FIG. 13, the emergency evacuation oxygen mask 100 according to an embodiment of the present disclosure may further include a notification mechanism 700 for sharing information of the user with other people. At this time, the information is intended to easily recognize a state of the user who is positioned at an accident site. For example, the information may be position information of the user, personal information of the user, physical health information of the user, or the like.

As a non-restrictive example, as illustrated in FIG. 14, the notification mechanism 700 may be provided with a light-emitting lamp 730 such as an LED lamp, so as to visually send a position of the user to a rescuer when the user is evacuating from fire.

As another example, the notification mechanism 700 may be provided with a speaker module (not illustrated) capable of generating a high-frequency emergency sound. Further, as illustrated in FIG. 15, a plurality of through-holes 740 may be provided such that the emergency sound is emitted to the outside. Through this, the notification mechanism 700 according to an embodiment of the present disclosure may audibly transmit the position of the user to the rescuer, thereby facilitating the rapid rescue activity performed by the rescuer.

As still another example, the notification mechanism 700 may be provided with a GPS module (not illustrated) so that position information of the user is transmitted and received. For example, a communication module (not illustrated) capable of transmitting information by using a frequency, such as RFID (radio-frequency identification), may be provided, so that information of the user may be transmitted by transmitting unique information related to the user to the outside. At this time, the information transmitted by the communication module may be, for example, health information such as high-risk disease information of the user, blood type information of the user, or real-time health information such as a blood pressure of the user, a pulse of the user, or the like that is received from a wearable device worn on the user.

Meanwhile, as illustrated in FIG. 14, the notification mechanism 700 may include a housing 720 with a predetermined volume, and may be formed in a relatively small size comparing to the upper cover 200 so as to be easily accommodated in the internal space of the upper cover 200 with the hood h.

In addition, in an inner portion of the housing 720 of the notification mechanism 700, a controller for controlling the light-emitting lamp 730, the speaker module, the GPS module, or the communication module that is described above and a battery with a predetermined capacity for supplying power to the plurality of modules may be mounted.

In addition, a physical button for initially generating an operation signal so as to activate the plurality of modules may be provided at the outer side of the notification mechanism 700. On the contrary, a sensor module (not illustrated) capable of automatically sensing air at the fire site and the like may be provided at the inside of the notification mechanism 700, so that controller may automatically activate the plurality of modules without the activation by the physical button that is described above.

In an embodiment of the present disclosure, as illustrated in FIGS. 13 and 15, the notification mechanism 700 may be provided with a penetration hole 750 through which a wire 710 fixed at a first side of the hood h and having a shape surrounding the hood h passes, so that the notification mechanism 700 is fixed to the hood h without being separated.

Hereinafter, a usage example of the emergency evacuation oxygen mask 100 according to an embodiment of the present disclosure will be described.

In an emergency situation, when the user holds the oxygen canister c or the lower cover 500 with one hand, the user may rotate the upper cover 200 in the clockwise direction with other hand. At this time, it is okay to rotate the oxygen canister c or the lower cover 500 in the counter-clockwise direction.

In the state as described above, as illustrated in FIGS. 7 and 8, the protruding member 420 inserted into the cutout portion 320 and positioned between the stopper 311 and the cam surface 312 of the second body 310 may be moved upwardly and horizontally toward the second side portion of the cutout portion 320 in the longitudinal direction.

In addition, the protruding member 420 positioned at the second side portion of the cutout portion 320 in the longitudinal direction is in contact with the rib 330 provided at the outer circumferential surface of the second body 310, and the movement of the protruding member 420 may be limited.

In addition, as illustrated in FIG. 10, the fastening protrusion 350 positioned at the first horizontal section d3 of the guide groove 440 may be moved to the second horizontal section d4.

In the state as described above, as the interval between the female coupling portion 300 and the male coupling portion 400 is reduced, the nozzle of the oxygen canister c is in contact with the ceiling surface of the female tubular portion 340 and is pressed.

Then, the nozzle of the oxygen canister c, the hole formed in the female tubular portion 340, and the oxygen supply port formed on the hood h are in communication with each other, and oxygen is capable of being supplied inside the hood h.

In the state as described above, as illustrated in FIG. 12, the user may separate the upper cover 200 from the second body 310 of the female coupling portion 300 by moving the upper cover 200 upward in the vertical direction. At this time, by the first groove 210 and the second groove 220, the upper cover 200 may be easily separated from the female coupling portion 300 without being interfering with the rib 330 provided at the second body 310 and the protruding member 420 disposed at the second side of the cutout portion 320 in the longitudinal direction.

When the upper cover 200 is separated from the female coupling portion 300, the hood h in a rolled state is exposed. As illustrated in FIG. 13, the user may unroll the hood h and may wear the hood h on the user's head, and the user may be supplied with oxygen.

For reference, the hood h may be formed of a material having an excellent heat-resistance characteristic and having an excellent flame retardant characteristic, and may be in a folded or a rolled state in the internal space that is formed by the upper cover 200.

For reference, a positive pressure is formed inside the hood h by oxygen provided from the oxygen canister c. Then, the user may take a spontaneous breath by using both an exhaled breath that is exhaled by the user and the pure oxygen supplied by the oxygen canister c.

For the inside space of the hood h to be formed with the positive pressure state and also for the user to smoothly take a breath at the inside space of the hood h, it is preferable that an internal surface of the hood h is spaced apart by a predetermined interval from the user's face or the user's head when the hood h is initially worn on. Therefore, it is preferable that the hood h is formed in a size and a shape that are spaced apart by the predetermined interval from the user's skin, rather than the size and the shape that are in close contact with the user's skin.

In addition, considering a place where the oxygen mask 100 is provided, an evacuation route, and the like, the oxygen canister c may have various sizes. Similarly, the amount of oxygen stored in the oxygen canister c, the degree of compaction of oxygen, and the discharging amount of oxygen may be set in consideration of the place where the oxygen mask 100 is provided, the evacuation route, and the like.

In addition, the oxygen canister c may discharge oxygen by using an orifice valve. A method of discharging a fluid by using the orifice valve has a simple structure and has low risk of failure, so that the orifice valve may be applied to safety equipment, relief equipment, and protective equipment.

In addition, a mask worn only around the user's mouth may be applied instead of the hood h surrounding the user's head and the user's entire face.

Although detailed exemplary embodiments according to the present disclosure have been described so far, obviously, various modifications may be made without departing from the scope of the present disclosure.

Therefore, the scope of the present disclosure should not be limited to the described exemplary embodiments, and should be determined not only by the scope of the claims to be described later, but also by the scope and equivalents of the claims.

What is claimed is:

1. An emergency evacuation oxygen mask comprising:
   a hood configured to be worn on a user's head;
   an oxygen canister configured to supply oxygen to the user who wears the hood;
   an upper cover in which the hood is accommodated;
   a female coupling portion coupled to a lower end portion of the upper cover and connected to an oxygen supply port that is provided at the hood; and
   a male coupling portion provided on the oxygen canister and coupled to the female coupling portion,
   wherein when the upper cover or the oxygen canister is rotated relative to each other, oxygen is discharged from the oxygen canister.

2. The emergency evacuation oxygen mask of claim 1, wherein when the upper cover is rotated in one direction which is relative to the oxygen canister, the female coupling portion is rotated in the one direction that is the same rotating direction of the upper cover, and the male coupling portion is moved upward by a rotating force generated from the female coupling portion, so that a nozzle provided on the oxygen canister is in contact with the female coupling portion.

3. The emergency evacuation oxygen mask of claim 2, wherein the male coupling portion comprises:
   a first body coupled to a circumference of an upper end portion of the oxygen canister;
   a protruding member protruding in a radial direction from an outer circumferential surface of the first body;
   a male tubular portion protruding upward from a top surface of the first body and surrounding the nozzle of the oxygen canister; and
   a guide groove provided at an outer surface of the male tubular portion.

4. The emergency evacuation oxygen mask of claim 3, wherein the female coupling portion comprises:
   a second body disposed on an upper portion of the first body;
   a cutout portion formed along an outer circumferential surface of the second body and into which the protruding member is inserted and caught;
   a rib protruding in the radial direction from the outer circumferential surface of the second body and connected to the upper cover;
   a female tubular portion protruding upward from a top surface of the second body and into which the male tubular portion is inserted; and
   a fastening protrusion provided at an inner circumferential surface of the female tubular portion and fastened to the guide groove.

5. The emergency evacuation oxygen mask of claim 4, wherein the upper cover comprises:
   a first groove formed at an inner circumferential surface of the lower end portion of the upper cover and into which the rib is inserted and accommodated;
   a second groove in communication with the first groove and providing a space where the protruding member inserted into the cutout portion is capable of being moved in a vertical direction; and
a long hole in communication with the second groove and providing a space where the protruding member is capable of being moved in a horizontal direction.

6. The emergency evacuation oxygen mask of claim 4, wherein the guide groove comprises:
a vertical section in which the fastening protrusion is moved in a vertical direction;
a curved section in communication with the vertical section and in which the fastening protrusion is moved in a curved direction;
a first horizontal section in communication with the curved section and in which the fastening protrusion is moved in a horizontal direction; and
a second horizontal section having a width thereof smaller than a width of the first horizontal section and in communication with the first horizontal section, the second horizontal section being configured to limit a movement of the fastening protrusion.

7. The emergency evacuation oxygen mask of claim 5, wherein the protruding member is inserted into the long hole via the cutout portion.

8. The emergency evacuation oxygen mask of claim 4, wherein the cutout portion is formed between an upper portion of the second body and a lower end portion of the second body, and the cutout portion is formed on the outer circumferential surface of the second body by being formed such that the cutout portion has a first end portion in a longitudinal direction of the cutout portion that is an open end at the lower end portion of the second body and a second end portion of the cutout portion in the longitudinal direction of the cutout portion is blocked by the rib on the upper portion of the second body.

9. The emergency evacuation oxygen mask of claim 8, wherein the second body comprises:
a stopper in contact with a first lateral side portion of the protruding member in the longitudinal direction of the protruding member and configured to limit a movement of the protruding member; and
a cam surface disposed to be spaced apart by a predetermined interval from the stopper and in contact with a second lateral side portion of the protruding member in the longitudinal direction of the protruding member when the upper cover is rotated in the one direction or the oxygen canister is rotated in a direction opposite to the one direction.

10. The emergency evacuation oxygen mask of claim 9, wherein the protruding member is disposed between the stopper and the cam surface, and then the protruding member is moved toward the second end portion of the cutout portion in the longitudinal direction of the cutout portion.

11. The emergency evacuation oxygen mask of claim 9, wherein when the protruding member is positioned at the second end portion of the cutout portion in the longitudinal direction of the cutout portion as the upper cover is rotated in the one direction or as the oxygen canister or a lower cover is rotated in the direction opposite to the one direction, the second side lateral portion of the protruding member in the longitudinal direction of the protruding member is in contact with the rib.

12. The emergency evacuation oxygen mask of claim 1, further comprising a lower cover configured to protect the oxygen canister, wherein an upper end of the lower cover is detachably coupled to a lower end of the male coupling portion.

13. The emergency evacuation oxygen mask of claim 1, further comprising a notification mechanism accommodated together with the hood inside the upper cover and configured to share information of the user with other person during an emergency situation, wherein the notification mechanism comprises at least one of a light-emitting lamp, a speaker module, a GPS module, and a communication module.

14. The emergency evacuation oxygen mask of claim 13, wherein the notification mechanism is formed such that a through-hole with a predetermined diameter is provided at a first side of the notification mechanism, and a wire fixed to the hood penetrates through the through-hole, so that the notification mechanism is fixed without being separated from the hood.

15. The emergency evacuation oxygen mask of claim 1, wherein a plurality of planes is disposed along an outer circumferential surface of the upper cover, and two planes that are adjacent to each other are disposed such that a predetermined angle is formed therebetween.

* * * * *